United States Patent [19]

Brinckmann et al.

[11] 4,245,360
[45] Jan. 20, 1981

[54] PARTIAL PELVIC PROSTHESIS

[76] Inventors: Paul Brinckmann, Rinscheweg 3; Jurgen Polster, Stettiner Str. 106, both of D-4400 Munster, Fed. Rep. of Germany

[21] Appl. No.: 16,962

[22] Filed: Mar. 5, 1979

[30] Foreign Application Priority Data

Mar. 6, 1978 [DE] Fed. Rep. of Germany ....... 2809556

[51] Int. Cl.³ .............................................. A61F 1/03
[52] U.S. Cl. .................................. 3/1.912; 128/92 B; 128/92 C
[58] Field of Search ...................... 3/1.912, 1.913, 1.9, 3/1.91; 128/92 C, 92 CA, 92 D, 92 B

[56] References Cited

U.S. PATENT DOCUMENTS

| 3,641,590 | 2/1972 | Michele | 128/92 B X |
| 3,698,017 | 10/1972 | Scales et al. | 128/92 C X |
| 3,740,769 | 6/1973 | Haboush | 128/92 CA X |
| 3,744,061 | 7/1973 | Frost | 128/92 CA X |
| 3,896,504 | 7/1975 | Fischer | 3/1.912 |
| 3,918,102 | 11/1975 | Eichler | 3/1.912 |
| 4,092,741 | 6/1978 | David | 128/92 CA X |

OTHER PUBLICATIONS

Scholher et al., "The Pelvic Endoprosthesis-An Alternative to Hemipelvectomy in the Case of Tumor Patients", Z. Orthop. 112 (1974) 968–970.

Primary Examiner—Clifford D. Crowder
Attorney, Agent, or Firm—Merchant, Gould, Smith, Edell, Welter & Schmidt

[57] ABSTRACT

A partial pelvic prosthesis comprising an implant piece (1) corresponding to that part of the pelvis to be resected, the piece (1) having a receiving space (2) for the acetabular fossa and connecting bores (8), and recess (15) for connecting prosthetic elements (7, 9, 10) whereby the elements can produce the required connection between the implant piece (1) and the pelvis. The piece (1) may contain threaded bores (12), (14) to receive screws (11) for adjustably fixing prosthetic elements (7, 9, 10) in bores (8) and recess (15).

4 Claims, 4 Drawing Figures

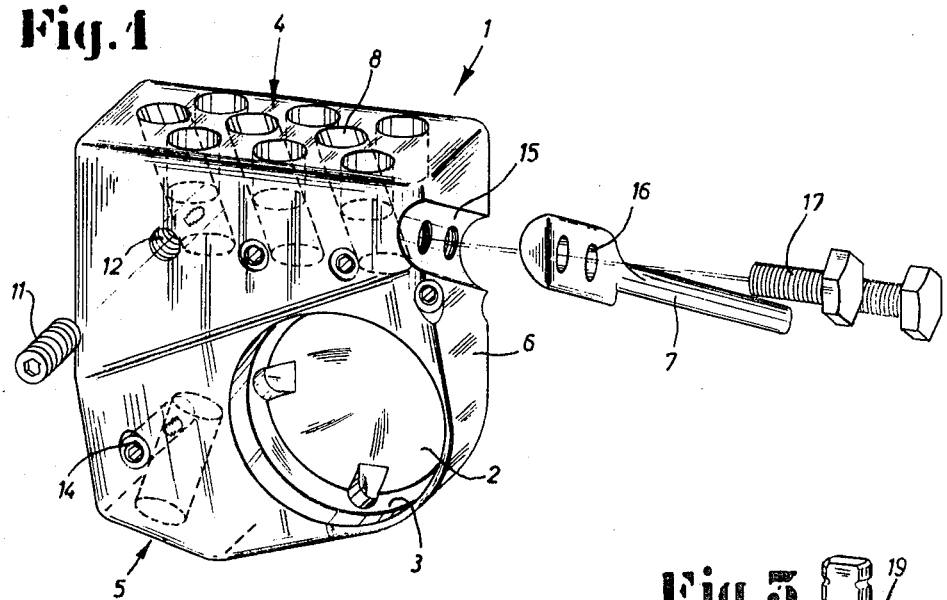
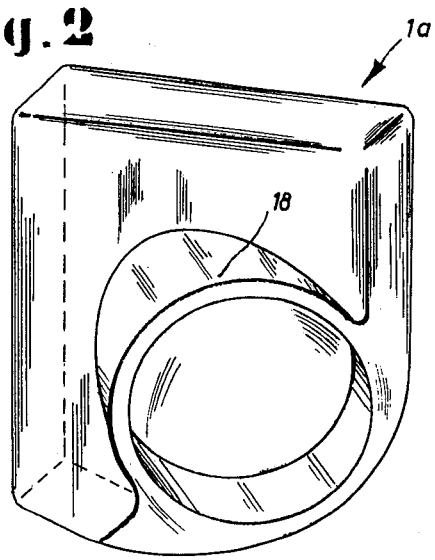
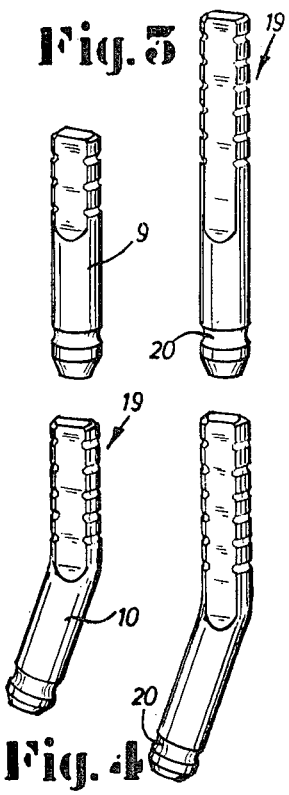

PARTIAL PELVIC PROSTHESIS

TECHNICAL FIELD

The invention relates to a partial pelvic prosthesis for receiving the acetabular fossa.

BACKGROUND OF THE INVENTION

In the journal "Orthopädie" 112 (1974, page 968–970), under the title "Die Beckenendoprothese—eine Alternative zur Hemipelvektomie bei Tumorpatienten" ("The Pelvic Endoprosthesis—an Alternative to Hemipelvectomy for patients suffering from tumours"), a pelvic endoprosthesis is described which consists of an implant piece which on the one hand has a recess for receiving the acetabular fossa and on the other hand is individually so matched to the pelvic shape of the patient that, as a result of this, as stable as possible a construction with solid anchoring to the healthy, remaining parts of the bone is achieved from the start after resection of the diseased parts of the pelvis. In this publication, a pelvic endoprosthesis is described and shown which was produced individually for the patient, in a five-week procedure, and which essentially consisted of four elements. These elements were the groove-shaped receiver, provided with bore holes, for the upper portion of the ilium, a tie-bar, the acetabulum and, finally, a seat and pubic bone support with the requisite fasteners.

These parts were constructed individually and welded to one another.

It is apparent that inexpensive and rapid manufacture of such large components which are to be constructed individually is not possible and that, in particular, operations which must be carried out rapidly cannot be carried out using pelvic endoprostheses of this type.

SUMMARY OF THE INVENTION

The object on which the invention is based is to provide a partial pelvic prosthesis with which the procedure described in the prior disclosure can be carried out without the disadvantages of this known pelvic endoprosthesis having to be accepted.

This object on which the invention is based is achieved by a partial pelvic prosthesis which is characterised by an implant piece which essentially corresponds to the part of the pelvis to be resected and has a receiving space for the acetabular fossa and connecting orifices for connecting pieces which are of different shapes and can be fixed in and/or at the connecting orifices and produce the connection between the implant piece and the residual parts of the pelvis.

Thus, the invention is based on the concept of providing a modular construction in which the basic component is the implant piece, which can be produced as prefabricated units in various sizes. This implant piece which forms the base component has a recess for receiving the acetabular fossa and is also provided with connecting orifices or means which now enable this base component to be individually matched to the particular pelvis of the patient and in particular also to be matched taking into account resected parts of the pelvis of different sizes.

The connecting pieces can be designed as pins and in particular the pin which produces the connection to the pubic bone is designed so that it can be shaped to match and these pins can be fastened in or on the implant piece and, furthermore, the possibility definitely exists of inserting additional parts as compensating units between the implant piece and the pins, in order thus to bridge the free spaces correspondingly obtained from relatively large resections and to enable fastening possibilities for the musculature and soft parts to be obtained.

BRIEF DESCRIPTION OF THE DRAWINGS

Illustrative examples of the invention are explained below with the aid of the drawing. The drawing shows in FIG. 1 an illustrative view of the implant piece according to the invention, in FIG. 2 a modified embodiment of an implant piece, in FIG. 3 a pin of straight design on an enlarged scale and in FIG. 4 a pin of bent design.

DETAILED DESCRIPTION OF THE INVENTION

In the drawing, 1 designates an implant piece in general and this piece possesses an indented recess 2 for receiving the acetabular fossa, which is not shown in the drawing, and it can be seen from the view in FIG. 1 that this receiving space for the acetabular fossa has an undercut 3, which is used for secure fixing of the acetabular fossa, for example by means of bone cement, within the receiving space 2.

In the upper part of piece 1, the surface 4 which faces towards the upper part of the ilium or sacrum can be seen; the surface designated 5 faces towards the ischium and the surface 6 serves to connect a pin which produces the connection to the pubic bone.

Cylindrical bores 8 are provided in the surfaces 4 and 5 (there being nine bores in surface 4 and one in surface 5 in the illustrative example shown) and the connecting pins 9 and 10 shown in FIGS. 3 and 4 can be fitted suction-tight into these bores; the pins can, however, have different lengths and different angling to those shown in the drawing in FIGS. 3 and 4. These pins are fixed in the bores 8 by means of the adjusting screws 11, which can be seen in the drawing and which are arranged in corresponding bores 12 and 14.

The pin 7, which produces the connection to the pubic bone, is fixed in a recess 15, which is clearly discernible in FIG. 1, this connecting pin being fixed by means of the fastening screws 17 which pass through the bores 16 in the connecting pin.

The embodiment of the implant piece 1a shown in FIG. 2 differs from the implant piece shown in FIG. 1 only in that it is of substantially narrower construction. An acetabulum support 18 is shaped so that adequate fixing of the acetabulum to be inserted can nevertheless be achieved.

A measure which is not shown in the drawing but which falls within the scope of the invention is that of inserting further additional implant pieces between the actual implant piece 1 or 1a and the connecting pins 7, 9 or 10, by means of which additional units the actual basic implant piece can thus be enlarged in order thus to enable resections of different sizes to be bridged despite uniform manufacture of the basic implant piece 1 or 1a.

At present, metal is proposed as the material for the implant piece, but it is, of course, possible to use appropriate plastics in this case also, and the connecting pins can also consist of an appropriate plastic. The connecting pin 7 which produces the connection to the pubic bone must be made of a material which permits corresponding bending.

Clearly discernible profiling 19 is provided on the pins and this serves to fix the pins well in the corresponding bone cement and by this means the corresponding connection to the natural, bony parts of the pelvis is achieved. The constriction 20 provided at the lower part of the connecting pin serves for positive fixing of the connecting pin in the bore 8 by the adjusting screw 11.

We claim:

1. A partial pelvic prosthesis comprising:
   (a) an implant piece adapted to be secured within the resected pelvis of a human patient and having a recess, adapted to receive an acetabular fossa, the first, second and third edges adapted to be apposed to the ilium or sacrum, the ischium, and the pubis respectively of said resected pelvis;
   (b) means for securing said implant piece in said pelvis comprising a plurality of connecting pins having first ends adapted to be cemented in holes bored in the bones of said pelvis, means in said edges of said implant piece for receiving the second ends of said pins, and means mechanically securing said second ends to said implant piece; and
   (c) said first edge of said implant piece including a plurality of orifices adapted to receive the second end of a connecting pin, said second end including a constriction and said orifices including cross bores and set screws to engage said constriction.

2. A prosthesis according to claim 1 in which said first ends of said pins are profiled.

3. A prosthesis according to claim 1 in which said third edge of said implant piece includes a transversely extending recess, and said second end of one of said pins is configured to be secured in said recess so that said pin extends generally orthogonal to said third edge.

4. A partial pelvic prosthesis comprising:
   (a) a generally flat implant piece adapted to be received within a resected pelvis in apposition with the ilium or sacrum, the ischium, and the pubis, said piece having upper and lower surfaces, front and rear faces, and first and second sides, said front face having a first recess comprising a concave bottom, undercut walls, for receiving an acetabular fossa, said upper and lower surfaces having a plurality of orifices therein, said first side including a second recess extending thereacross from said front face to said rear face and having a plurality of bores therein, said front face including additional bores aligned to intersect with bores of said plurality for receiving threaded fasteners;
   (b) a plurality of connecting pins configured at one end to fit within said orifices and at the other end for securement in said ilium or sacrum and said ischium to hold said implant piece within the pelvis, said pins being profiled at one end and having a constriction at the other end; and
   (c) a connecting pin for attachment at one end to the pubis and at the other end to said implant piece, said pin having a flange at one end configured for reception in said second recess and including a plurality of holes for alignment with said bores in said first recess to receive fastener means for attaching said pin to said implant piece.

* * * * *